United States Patent [19]

Royer

[11] 4,326,009
[45] Apr. 20, 1982

[54] POLYMERIC PARTICULATE CARRIER

[76] Inventor: Garfield P. Royer, 100 Howard St., Worthington, Ohio 43085

[21] Appl. No.: 169,264

[22] Filed: Jul. 15, 1980

Related U.S. Application Data

[63] Continuation of Ser. No. 936,845, Aug. 25, 1978, abandoned, and a continuation-in-part of Ser. No. 819,283, Jul. 27, 1977, abandoned.

[51] Int. Cl.³ .............................................. B32B 5/16
[52] U.S. Cl. .................................. 428/407; 428/402; 428/403
[58] Field of Search ...................... 428/407, 403, 402

[56] References Cited

U.S. PATENT DOCUMENTS 3,352,800 11/1967 Smith .................................. 428/407

Primary Examiner—Marion McCamish

[57] ABSTRACT

A polymeric carrier is disclosed having a particle size such that the largest dimension thereof is less than about 8 mm and the smallest dimension is at least about 0.1 mm. The carrier comprises a plurality of polymeric segments containing chemically modifiable groups on the surface. The segments are united into a coherent, stable porous matrix by means of cross-links between segments. The matrix defines at least one cavity of predetermined size, and the particle size of the carrier, the porosity of the matrix and the presence of the cavity combine to provide desirable liquid compatibility and diffusional characteristics.

12 Claims, 5 Drawing Figures

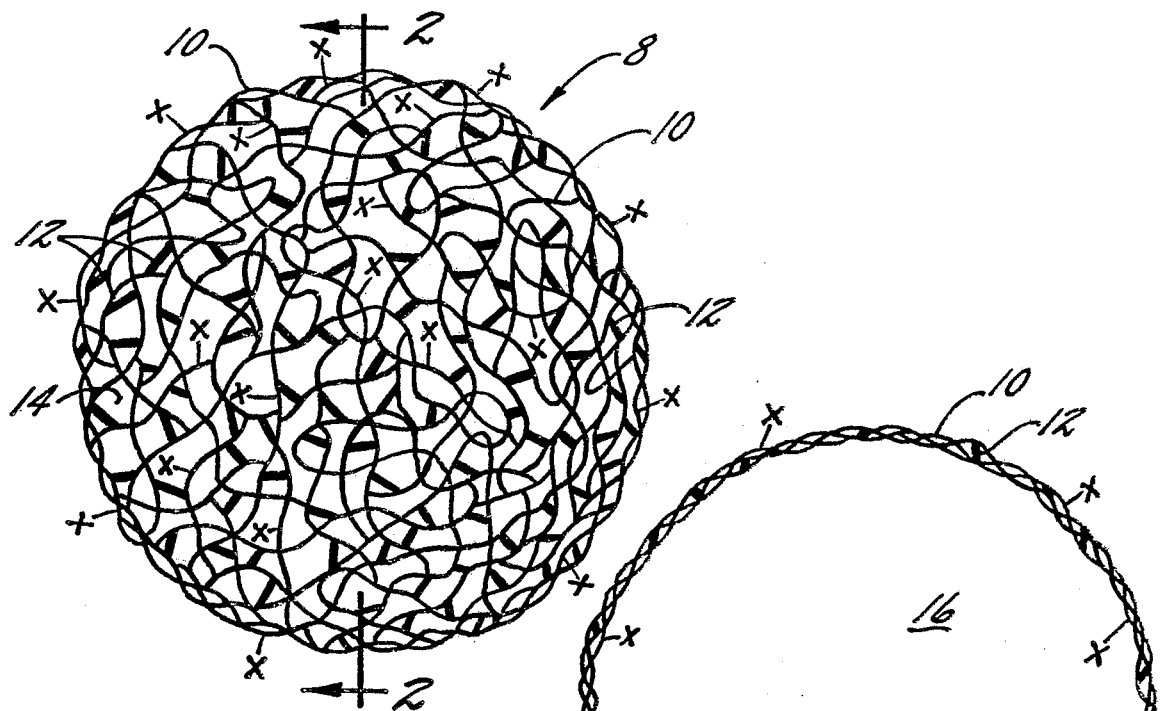
Fig. 1.
Fig. 2.
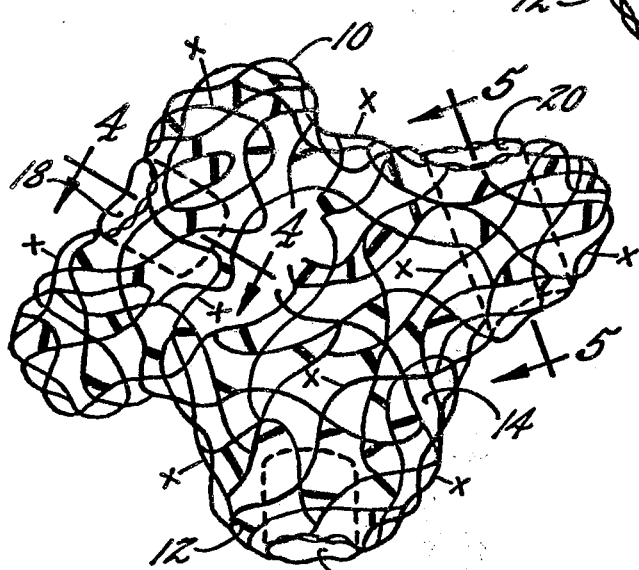
Fig. 3.
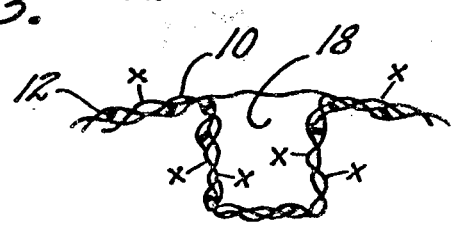
Fig. 4.
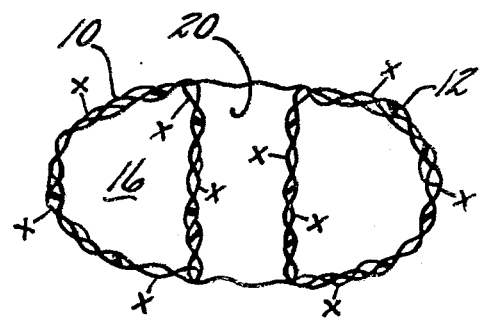
Fig. 5.

POLYMERIC PARTICULATE CARRIER

This is a continuation of application Ser. No. 936,845 filed Aug. 25, 1978, abandoned and is a continuation-in-part of my application Ser. No. 819,283, filed July 27, 1977, entitled Polymeric Particulate Carrier abandoned.

The present invention relates to polymeric carriers containing chemically modifiable groups and, more particularly, to porous carriers which provide desirable fluid compatability and diffusional characteristics.

Carriers, sometimes referred to as solid resins or supports, are currently being used in a number of applications including the solid phase synthesis of organic compounds such as polypeptides, enzyme immobilization, chromatography, ion-exchange, and solid phasesequencing of proteins, peptides and nucleic acids. The carriers are generally polymeric or inorganic and contain covalently attached chemically modifiable groups, the nature of the groups depending upon the particular application for which the carrier is intended. In application, the modifiable groups may undergo covalent or ionic modification. Advantages accompanying the use of carriers are, among others, ease in separation and purification of synthetic intermediates, minimization of the likelihood that valuable products may be lost, and enhanced stability and durability of catalytic substances attached to the carrier.

Heretofore, limitations accompanying the use of carriers have centered on their liquid compatibility and diffusional characteristics. Ideally, a carrier should be compatible with both aqueous and organic liquids and, particularly, polar aqueous or organic solvents. As to diffusion, liquid should be able to freely permeate the carrier so as to provide access to the modifiable groups at the interior.

The problem has resided in obtaining a carrier wherein both desirable liquid compatibility and diffusional characteristics are present in combination with good mechanical and chemical stability. For example, the customary carrier for solid-phase peptide synthesis is a chemically modified polystyrene resin. To provide desirable diffusional characteristics, this material must be swollen with a non-polar organic solvent. In turn, this has limited the solid-phase synthesis of polypeptides to those techniques which are accomplished in an organic environment. Another customary carrier is derivatized porous glass. While this carrier is compatible with either water or organic solvents, optimum stability characteristics have been difficult to achieve.

Accordingly, the principal objective of the present invention is to provide a carrier which is useful in applications such as heretofore identified, and which possesses both desirable liquid compatibility and diffusional characteristics in combination with good mechanical and chemical stability. Other objectives and advantages of the present invention will become apparent upon reading the following description of the invention taken in combination with the attached drawing wherein FIGS. 1 and 3 schematically illustrate embodiments of carriers of the invention, FIG. 1 is a sectional view taken along line 2—2 of FIG. 1. FIG. 4 is a partial sectional view taken along line 4—4 of FIG. 3, and FIG. 5 is a sectional view taken along line 5—5 of FIG. 3.

In accordance with the present invention, a carrier of predetermined particle size is provided which is formed from a plurality of polymeric segments having chemically modifiable groups on their surface. The segments are united into a coherent, stable porous matrix by means of cross-links between them. The matrix defines at least one cavity of predetermined size. The particle size of the carrier, the porosity of the matrix and the presence of the cavities combine to provide desirable liquid compatibility and diffusional characteristics.

Being of known size, porosity, and density, the carriers can be combined to form the particulate assemblies having tailored diffusional characteristics. Such assemblies are comprised of a plurality of the carriers as individual particles, and can either be a homogeneous population of substantially identical particles or a mixture of particles having different, but known, size, porosity and density.

Turning to the drawing, FIG. 1 schematically illustrates a carrier 8 generally in the shape of a hollow spherical particle, the surface of which contains a plurality of polymeric segments 10 which contain chemically modifiable groups x exposed on the surface thereof. In order to unite the polymeric segments 10 into a coherent matrix to provide a self-supporting stable particulate structure with desirable liquid compatibility features, the segments 10 are joined together by means of chemical cross-links 12 between the segments. As illustrated, the matrix of segments and cross-links contains open spaces 14 such that, although the particulate carrier is mechanically and chemically stable, the carrier is nevertheless porous to liquids. Referring specifically to FIG. 2, the matrix formed by the polymer segments 10 and the cross-links 12 defines a cavity 16. As will be discussed hereafter, the size of the cavity 16 can be predetermined and, accordingly, the carrier can be fashioned with desirable fluid diffusional characteristics.

Turning now to FIGS. 3-5, a further schematic illustration of a particulate carrier constructed in accordance with this invention is illustrated. In this embodiment, three additional cavities, 18, 20, and 22, are shown. In turn, each of these cavities is defined by the coherent, porous matrix formed by the polymer segments 10 and cross-links 12 between the segments. As with FIGS. 1 and 2, the segments contain chemically modifiable groups x exposed on the surface of the segments.

A useful method for forming polymeric particulate carriers of the instant invention involves contacting a polymer, dissolved in an appropriate solvent, with a dissolvable, generally inorganic, particulate solid support such that the polymer is adsorbed to the surface of the support particles. After removing any excess polymer which is not adsorbed, the polymer is cross-linked and, thereafter, the supporting member is dissolved to leave the carrier. Gentle agitation while the support is suspended in a fluid should be employed during the cross-linking reaction so that cross-linking only occurs between polymer segments adsorbed on individual support particles, and not between polymer segments adsorbed on different particles.

The size, shape, and porosity of the support is selected in accordance with the desired size, shape and cavity configuration of the carrier. It can be solid, as when a carrier with a single cavity such as illustrated in FIG. 1 is desired, or porous where two or more cavities are to be present (FIG. 3).

An important aspect of this invention resides in the fact that the carrier is particulate and that its particle size and the size of the cavity(s) contained therein are predeterminable; these factors, in combination with the degree of cross-linking achieved, influencing the carrier's liquid diffusional characteristics. In accordance with this invention, particle size will be such that the largest dimension of the carrier will be less than about 8 mm and, preferably, less than about 3.0 mm. In general, the smallest dimension will be at least about 0.1 mm.

Where the carrier contains only a single cavity, i.e., formed from a solid support particle, the size of that cavity will closely approximate the size of the dissolvable support particle since the matrix itself is generally very thin, e.g., less than about 200 Å thick. However, where more than one cavity is present, cavity size cannot be directly related to the particle size of the support. And, in this latter instance, cavity size is best defined by the smallest dimension of the cavities which, for the present invention, is at least about 50 Å and, preferably, at least about 300 Å. In general, the ratio of carrier polymer to void space is less than about 10% by volume and, preferably, less than about 5%.

Turning to the polymers useful in forming carriers of the invention, the important aspects thereof are that the polymer can be adsorbed to a support, that, after adsorption, it can be cross-linked into a porous matrix, and that it contains or can be fashioned to contain, the desired chemically modifiable surface group. For most applications, the polymer will, prior to adsorption, contain both the functional groups needed to achieve cross-linking and the groups which are intended for chemical modification in the end use application.

For example, in the event that the carrier is to be used in applications such as peptide synthesis or sequencing or enzyme immobilization, wherein the chemically modifiable group is an amine, then polymers having free reactive amine groups are most useful for the carrier. By selecting an appropriate cross-linking reagent, such as a dialdehyde, formaldehyde, phosgene, thiophosgene, etc., a portion of the amine groups on the polymer can be involved in the cross-linking reaction leaving other of the amine groups for the desired attachment to the carboxyl group of an amino acid, peptide fragment or enzyme. A particularly useful polymer is polyethyleneimine because of the large number of reactive primary amine groups in the polymer.

Proteins themselves are useful polymers where chemically modifiable amine groups are desired, the protein again being conveniently cross-linked on a support with a dialdehyde. Human serum albumin (HSA) is considered to be an especially useful protein for this application. As a particulate carrier, this protein which is biodegradable may find use as an encapsulating device for the sustained in-vivo release of biologicals such as drugs, hormones, and the like.

Polyamide (partially hydrolyzed) is a further type of useful polymer. This polymer contains both free acid groups and free amine groups. Thus, depending on the cross-linking agent utilized, the carrier can contain, as the chemically modifiable group, either an acid or amine. If an amine is desired, then a diamine can be used as the cross-linking agent. If, on the other hand, chemically modifiable acid groups are desired, then a dialdehyde, formaldehyde, etc. can be used for cross-linking.

An advantage accompanying the use of a polymer such as a polyamide having dual functionality is that the availability of the desired chemically modifiable group is not effected by the cross-linking operation, and as a result, large excesses of the cross-linking reagent can be employed. This is not the case with respect to the use of polymers wherein cross-linking is through the same type of group which is also to be available for chemical modification during use of the carrier. In this latter instance, the degree of cross-linking effected must be controlled so as to have a sufficient number of chemically modifiable groups left in the carrier so that it is useful for its intended application.

As will be appreciated, a number of other polymers are useful in forming the carriers of the instant application. Where chemically modifiable OH groups are desired, polyvinyl alcohol or dextran can be used, and cross-linking accomplished with, for example, a dihalide or diisocyanate. Where free acid groups are required, in addition to the above mentioned polyamide polymer, polyacrylic acid and polyethylene-maleic anhydride are also useful. In these latter instances, a diamine can be used for cross-linking.

While the foregoing discussion has centered on the use of polymers which, as prepared, contain the chemically modifiable group, the invention also embraces polymeric particulate carriers wherein the modifiable group is introduced after polymer formation. Carriers containing groups chemically modifiable by ionization and useful in ion exchange chromatography are examples. Thus, if the carrier contains free amine groups, it can be directly used as a basic ion exchange resin. However, by reacting the modifiable amine groups with, for example, succinic anhydride, a carrier useful as an acidic ion exchange resin is provided.

Turning to the dissolvable support, particularly useful materials are alumina, silica and glass. These materials are commercially available or can be easily prepared, in a variety of shapes and with controlled pore size so as to make the volume of the cavities in the polymeric carrier easily determinable. With these materials, removal from the cross-linked polymer can be accomplished by dissolution using solvents which do not adversely affect the cross-linked polymer. Glass and silica can be conveniently dissolved with a strong base such as sodium hydroxide while alumina can be dissolved with a strong acid such as HCl.

The following examples illustrate the present invention. All parts and percentages are by weight unless otherwise indicated. Temperature is in degrees centigrade.

EXAMPLE I 400 ml of an 8.3% solution of polyethyleneimine (PEI-600 Dow) in methanol was mixed with 100 ml of porous approximately spherical alumina beads (350–500 Å pore size, about 1 mm diameter particle size). Trapped air was removed by vacuum and the mixture gently agitated for 30 minutes. The beads were washed with 5 portions of methanol (200 ml each) and then dried in vacuo at room temperature. The beads (25 g, containing adsorbed PEI), were reacted at room temperature with 250 ml of 0.4% aqueous glutaraldehyde to cross-link the polymer. Gentle agitation accompanied the cross-linking reaction. Trapped air was removed and the reaction was continued for 30 min. The glutaraldehyde solution was then replaced with 100 ml of an 8.3% solution of PEI in methanol to react with any glutaraldehyde which failed to completely react, and after 15 min. of gentle agitation, the PEI solution was replaced with 100 ml of methanol. A total of 2 g of NaBH$_4$ was added in small increments over a period of 30 min. to form stable cross-links. The beads were then washed and dried as above described. A PEI carrier was then produced by treatment of 10 grams of the beads with 100 ml of 1N HCl for approximately 15 min. at room temperature. The acid was decanted and replaced with a second 100 ml-portion of 1N HCl. After 30 min. the PEI-carrier containing amine modifiable groups was then washed with water and methanol and then dried in vacuo at room temperature.

To demonstrate the use of this carrier in connection with enzyme-like catalysis, histidyl residues were introduced onto the carrier by reaction of the amine groups with the nitrophenyl ester, Boc-His ($^{Im}$DNP)-ON$_p$, as follows: After treatment with 0.2 ethanolic-KOH, the PEI carrier (4 ml settled volume) was mixed with 100 mg of the nitrophenyl ester and 2 equivalents of triethylamine in 5 ml of dry dioxane, and the mixture was rotated for 12 hr at 60°. The boc group was removed with 30% TFA in CHCl$_3$ (5 ml, 12 hr, at 25°). The DNP group was removed by thiolysis (0.1 M mercaptoethenol, pH 9, 12 hr, 25°). After hydrolysis (6N HCl, 110°, 24 hr), amino acid analysis was done. The result was 0.4 meg His/g. Lauroyl groups were then introduced by treatment with nitrophenyllaurate (500 mg in 25 ml of dioxane, containing 0.2 ml of triethylamine) for 72 hours at 70°. A sample which contained no histidyl residues was lauroylated in the same way and used as a control.

p-Nitrotrifluoroacetanilide was hydrolyzed using the following conditions: 0.01 M N-ethylmorpholine-HCl buffer, pH 8.1, 40 ml of substrate, $10^{-4}$M; 25°; 7 mg of catalyst. At timed intervals samples were removed for analysis by means of a syringe fitted with a tube covered by nylon net. The second-order rate constants for hydrolysis catalyzed by imidazole, and the lauroyl-histidyl-PEI-carrier were estimated to be 0.007 $M^{-1}s^{-1}$ and 1.7 $M^{-1}s^{-1}$, respectively. The rate constants were calculated on the basis of total imidazole content in both cases. Carriers modified only with lauroyl groups do not produce a rate enhancement over background. The sizable rate enhancement about 230 times for the lauroyl, histidyl modified carrier is believed to be attributable to the lauroyl groups being able to bind substrate in close proximity to imidazole ring of histidine which, in turn, is obtainable because of the desirable fluid diffusion characteristics of the carrier.

The enzyme, pepsin, was also immobilized on the PEI-carrier of Example I by washing 400 mg of the carrier with a coupling buffer (0.13 N pyridine-HCl, pH 4.5) and then adding the carrier to a solution (3.5 ml) of pepsin (2 mg/ml) in the coupling buffer. The suspension so formed was then combined with 14 mg of the water soluble carbodiimide, 1 -cyclohexyl-3-(2-morpholinoethyl) carbodiimide-metho-p-toluene sulphonate. This suspension was maintained at pH 4.5 for 1.5 hrs at room temperature and then rotated overnight at 0-4°. After successive washing with 0.5 l portions of 1 mM HCl, 0.5M KCl and 1 mM HCl, the PEI-immobilized pepsin exhibited high activity.

EXAMPLE II

Controlled-pore glass (10 g, 550 A, 40/80 mesh) and 100 ml of polyethyleneimine (50,000 MW, 8% in methanol) were placed in a round bottom flask. A vacuum was applied for 10 min with rotation of the flask. After an additional hour of rotation, the solution was decanted. The beads were washed twice with methanol (at least 100 ml each time) and dried in vacuo for 24 hr. The polymer layer was cross-linked with glutaraldehyde using the following conditions: 80 ml of N-ethyl morpholine (0.1M, pH 8.0) containing 0.2% glutaraldehyde, 5 min evacuation, rotation overnight, and washing with buffer. The inorganic core was removed by treatment with 250 ml of 2 N NaOH for 24 hrs to provide the carrier.

EXAMPLE III

Polyvinylimidazole (PVI) was absorbed to porous glass beads as described in Example II, and cross-linking accomplished with diazotized 4, 4' sulfonyl dianiline. To 5 g of PVI-Glass suspended in 20 ml of 0.1 phosphate buffer (pH 0.8), 70$\mu$ moles of diazonium salt was added. The mixture was tumbled gently at 0-4° for 90 min. The beads were washed with 3, 200-ml portions each of the following: phosphate buffer, H$_2$O and methanol. The material was dried in vacuo overnight. Removal of the inorganic core was accomplished with base as described in Example II.

EXAMPLE IV

A solution of HSA (about 1% in water, 50 ml) was suspended with 100 ml of alumina beads as described in Example I; the beads having first been washed with distilled water and trapped air removed by vacuum. After about 30 minutes of gentle agitation, the procedure described in Example I was continued except that about a 1% aqueous solution of HSA was used to "cap" any glutaraldehyde which failed to react. Removal of the alumina support and recovery of the cross-linked HSA carrier was as described in Example I.

While the present invention has been described in connection with certain preferred embodiments, it is to be understood that it is not to be limited to only those embodiments. On the contrary, it is intended to cover all modifications and alternatives falling within the spirit and scope of the invention as expressed in the appended claims.

I claim:

1. A polymeric carrier having a predetermined particle size such that the largest dimension thereof is less than about 8 mm and the smallest dimension is at least 0.1 mm, said carrier comprising a plurality of polymeric segments containing chemically modifiable groups on the surface thereof, said segments being united into a coherent, stable porous matrix by means of cross-links between segments, said matrix defining at least one cavity of predetermined size, the particle size of said carrier, the porosity of said matrix and the presence of said cavity combining to provide desirable liquid compatability and diffusional characteristics.

2. The carrier of claim 1 having a particle size such that the largest dimension is less than about 3.0 mm.

3. The carrier of claim 1 wherein the polymeric segments are polyetheneimine.

4. The carrier of claim 3 wherein the cros-links are formed with a dialdehyde.

5. The carrier of claim 4 wherein the dialdehyde is gluteraldehyde.

6. The carrier of claim 4 having a particle size such that the largest dimension is less than about 1.5 mm.

7. A method of forming a polymeric particulate carrier as set forth in claim 1 comprising adsorbing polymer segments onto a dissolvable particulate solid support, cross-linking said segments into a stable matrix while said segments are adsorbed to said support and, thereafter, dissolving said support to provide the carrier.

8. The method of claim 7 wherein the solid support is alumina, silica or glass.

9. The method of claim 8 wherein the polymer is polyethyleneimine.

10. The method of claim 9 wherein cross-linking is accomplished with gluteraldehyde.

11. A particulate assembly comprised of a plurality of individual polymeric carriers as set forth in claim 1.

12. The particulate assembly of claim 11 wherein each of the carriers is substantially identical to thereby provide a homogeneous population of individual particles.

* * * * *